US00PP10936P

United States Patent [19]

McAfee, Jr.

[11] Patent Number: Plant 10,936

[45] Date of Patent: Jun. 1, 1999

[54] ELAEAGNUS PLANT NAMED 'GOLDEN'

[76] Inventor: George McAfee, Jr., 5540 Farmer, Houston, Tex. 77020

[21] Appl. No.: 08/897,299

[22] Filed: Jul. 21, 1997

[51] Int. Cl.[6] ..... A01H 5/00

[52] U.S. Cl. ..... Plt./226

[58] Field of Search ..... Plt./33.1, 54.1, Plt./226

*Primary Examiner*—Howard J. Locker
*Assistant Examiner*—Kent L. Bell
*Attorney, Agent, or Firm*—Martin L. McGregor

[57] ABSTRACT

The invention is a novel cultivar of Elaeagnus. The leaf color is golden yellow on the upper side surface and greyed yellow on the underside surface. The mature leaves curl inwardly on the upper surface leaving the underside of the leaf as the predominant visible surface and color of the bush. The small flowers are funnel-shaped, yellowish white fragrant and ½ inch long. The flowers are borne clustered in groups. The plant is an ornamental shrub which may be used as a color accent in landscaping.

1 Drawing Sheet

TECHNICAL FIELD

The present invention relates to a new and distinct variety of Elaeagnus plant, which was discovered in 1996 as a sport branch growing on cultivated property in Houston, Tex. More particularly, the present invention relates to a novel cultivar of Elaeagnus having unusual and distinctive characteristics.

BACKGROUND OF THE PLANT

The Elaeagnus plant is of the family elaeagneae. A patented Elaeagnus is disclosed in U.S. Plant Pat. No. 7,750 which claims a new variety of olive with a distinctive growth habit. The parent of the novel cultivar in this application is a variegated Elaeagnus scrub with dark green centered leaves bordered by a yellow edge. The parent is 5 to 6 feet high and 5 to 6 feet wide. The leaves are alternate, simple and entire. The leaf shape is elliptic to oblong ovate and varies from 1 to 2 inches in length.

SUMMARY OF THE INVENTION

The new sport was discovered as a branch on the variegated Elaeagnus purchased from a commercial nursery in Houston, Tex. and under cultivation at 2805 Arbor in Houston, Tex. The leaf color of the novel cultivar is golden yellow on the upper side surface and greyed yellow on the underside surface. The mature leaves curl inwardly on the upper surface leaving the underside of the leave as the predominant visible surface and color of the bush. The small flowers are funnel-shaped, yellowish white, fragrant and ½ inch long. The flowers are borne clustered in groups in the leaf axil. The globose fruit is silvery mixed with brown scales turning red while ripening. The fruit is ¼ to ⅓ inch in diameter. This plant generally has a habit which is spreading.

DESCRIPTION OF THE PREFERRED PLANT VARIETY

Figure 1:
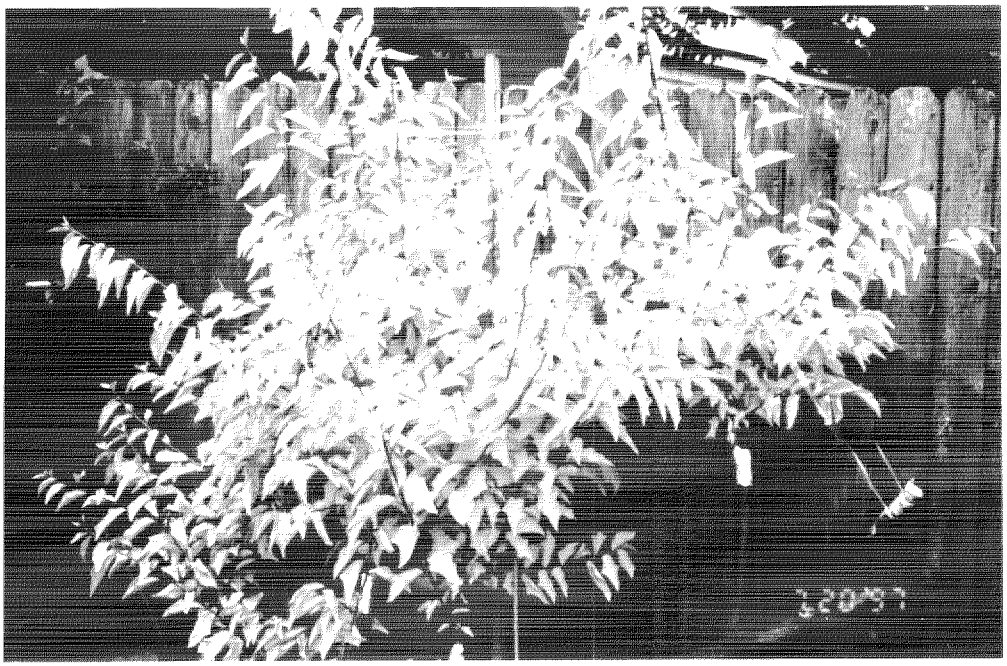
FIG. 1 shows the new Elaeagnus plant in full summer foliage.

In this invention, my new Elaeagnus plant is a plant with a unique golden color quite unlike the parent variegated plant, which has dark green with yellow edged leaves. The new plant also differs from the parent in leaf size and shape as set out in detail below. The plant is believed to be *Elaeagnus pungens.*

Asexual reproduction of my new plant was performed at 5538 Farmer, Houston, Tex. Zone 9, by taking softwood cuttings and grafting them into established Elaeagnus root stocks. The 6 grafted plants grew to over 4.5 feet in height in one growing season. The cuttings exhibited the same form, and distinctive color as the original sport branch which is quite different from the rest of the parent plant. Successful reproduction shows the coloration and distinctions are established and transmitted through succeeding propagation of the plant.

The following is a specific description by way of a specific example of the new Elaeagnus cultivar, color terminology being referenced to the nearest match in The Royal Horticultural Society Colour Chart, London, England, 1995, hereinafter referred to as R.H.S.

Leaves: The leaves are alternate, simple and entire. The leaves have a shape that is elliptic to oblong-ovate, with crisped margin. The length of the leaf blade varies from 1 to 4 inches and the width varies form ¾ to 1½ inches. The leaves are much larger than the parent leaves which are typically 2 to 2.5 inches in length. The leaf tip is obtuse to short-acuminate, and the leaf base is rounded to broadly cuneate. The small new leaves appear at the ends of the branches and normally have brown scales (R.H.S. Brown Group 200C) on both surfaces with a background color near R.H.S. Green Group 138B on the upper surface and R.H.S. Greyed Green Group 192B on the under surface. The color changes with leaf age and size as the leaves mature to a golden yellow and curled shape. The maturing leaf passes through light lime greens such as R.H.S. Yellow Green Group 144B with an under surface of R.H.S. Greyed Green Group 195C as it ages and the scales become less dense as the leaf grows. The mature leaf is golden (R.H.S. Yellow Group 11A) on the upper side surface and greyed yellow (R.H.S. Greyed Yellow Group 158A) on the underside surface in mid-season and is translucent.

Shrub: The plant at maturity may have a height of approximately 9 feet with the spread being approximately equal to the height, the overall appearance of the plant being spreading and symmetrical. The leaf bearing stems have a background greyed brown color (R.H.S. Greyed Brown Group 199D) covered with brown spots (R.H.S. Brown Group 200C).

Flower: The flowers occur in September to October in Zone 9 in the leaf axil. The flowers are clustered in groups of 1 to 3 or more, and are fragrant. Each flower is ½ inch long, tubular or funnel-shaped with the tube much longer than the limb. The 4 short-stalked stamens are attached to the top of the tube, which is yellowish white in color inside (R.H.S. White Group 155A), and covered with silver scales on the outside. The style is scaly and the 4 lobes are expanded.

Fruit: The fruit is a single-seeded drupe which is globose or sub-globose to ovoid in shape. The fruit color is silver mixed with brown scales, finally turning red (R.H.S. Red Group 44A) when ripe in November to December. The fruit is prolific, nearly encircling the stem, on ¼ to ½ inch long stalks. The fruit is each ¼ to ⅓ inch in diameter.

The characteristic of the new plant which distinguishes it from other Elaeagnus is its distinctive color as illustrated in FIG. 1.

I claim:

1. A new and distinct cultivar of Elaeagnus plant, substantially as herein shown and described.

* * * * *